United States Patent
Doms et al.

[11] Patent Number: 5,812,241
[45] Date of Patent: Sep. 22, 1998

[54] COMPACT REFRACTOR FOR SUBJECTIVE EXAMINATION OF HUMAN EYES

[75] Inventors: Manfred Doms; Ulrich Fischer, both of Saalfeld, Germany

[73] Assignee: Block Medizintechnik GmbH, Saalfeld, Germany

[21] Appl. No.: 596,383

[22] PCT Filed: Jun. 17, 1994

[86] PCT No.: PCT/DE94/00697

§ 371 Date: Feb. 16, 1996

§ 102(e) Date: Feb. 16, 1996

[87] PCT Pub. No.: WO95/05113

PCT Pub. Date: Feb. 23, 1995

[30] Foreign Application Priority Data

Aug. 19, 1993 [DE] Germany .......................... 43 27 896.5

[51] Int. Cl.⁶ .................................................. A61B 3/100
[52] U.S. Cl. .......................... 351/217; 351/216; 351/235
[58] Field of Search .................................... 351/217, 216, 351/205, 200, 246, 235

[56] References Cited

U.S. PATENT DOCUMENTS

| | | |
|---|---|---|
| 1,666,406 | 4/1928 | Clement et al. . |
| 2,968,213 | 1/1961 | Wright et al. . |
| 3,498,699 | 3/1970 | Wilkinson . |
| 4,606,624 | 8/1986 | Wood . |

FOREIGN PATENT DOCUMENTS

| | | |
|---|---|---|
| 0070333A2 | 1/1983 | European Pat. Off. . |
| 0186953A3 | 7/1986 | European Pat. Off. . |
| 2901459A1 | 7/1980 | Germany . |
| 3037466A1 | 5/1981 | Germany . |
| 3524498A1 | 1/1986 | Germany . |
| 402516 | 12/1933 | United Kingdom . |

*Primary Examiner*—Hung X. Dang
*Attorney, Agent, or Firm*—Jordan and Hamburg

[57] ABSTRACT

A compact and precise phoropter of low requirements as to material and favorable as to kinematics comprises two observation channels in each of which a plurality of equal sized disks are rotatably and coaxially arranged about an axle, each of said disks being provided with a number of element sites where spherical lenses, cylindrical lenses, cross cylinders and further optically effective accessory elements are located. At least the cylindrical lenses are seated for rotation on said disks and are provided with first drive wheels, the diameters of the latter being substantially equal to the diameter of a second drive wheel rotatable with the axle and being associated to the respective disk. The diameters of the entire disks are determined by the diameters of the first and the second drive wheels and are at least three-fold the diameter of the first drive wheels.

15 Claims, 5 Drawing Sheets

| Disk | | | | Element Site | | | |
|---|---|---|---|---|---|---|---|
| 23 | 0 | -9 | -18 | -27 | +18 | +9 | |
| 24 | 0 | +1.5 | +3 | +4.5 | -3 | -1.5 | |
| 25 | 0 | +0.25 | +0.5 | +0.75 | -0.5 | -0.25 | |
| 26 | 0 | -1.25 | -2.5 | -3.75 | -5 | | Centering Means |
| 27 | 0 | -0.25 | -0.5 | -0.75 | -1 | | Occluder |
| 28 | 0 | Spherical-Lens -0.125 | A-shaped Pol-filt. | V-shaped Pol-filt. | Maddox-Cylinder | Color Filter | Aperture |
| 29 | 0 | | Cross-Cylinder ±0.25 | Cross-Cylinder ±0.5 | | | Rotation Prism |

COMPACT REFRACTOR FOR SUBJECTIVE EXAMINATION OF HUMAN EYES

BACKGROUND OF THE INVENTION

The invention relates to a phoropter according to the kind of art as disclosed in the claims for testing the human eye for determining vision aids.

Various modifications of phoropters are conventionally employed for subjectively determining the refraction of the human eye. Typically, they consist of a number of disks for supporting optical elements which permit various combinations of elements for determining the deficiency of sight of the human eye. A known phoropter is constituted of two lens supporting disks which are arranged for rotation about at least one axis (common axis) in a housing (refer to DE 3524498 A1), one disk being provided with a large number of lenses and the other disk with a low number of lenses, located at definite sites of elements. Since the disk comprising the large number of lenses has to be of large diameter, due to the geometrical and optical conditions, and since the lenses of both disks have to cooperate in the common observation path the diameter of the disk supporting the lower number of elements is determined accordingly. Hence, a phoropter of considerable dimensions and expenditures for material results.

This proves to be a considerable disadvantage when such a phoropter has to be mechanized or automated since the drive and scanning means require additional space in the vicinity of the disks (refer to EP 0 070 333 A2 and DE 30 37 466 A1).

To avoid that the patient is subject to disturbances the phoropters are generally required to have a housing width at the dioptric passage, i.e. the length of the observation channels, as short as possible. For example, with a leading phoropter producer this length is 27 mm, otherwise the housing width is 100 mm. On the one hand, this condition requires a considerable low number of lens and prism disks and an increase of their diameters. On the other hand, a considerably large part of the face of the patient should be visible to involve the patient's features in the course of an examination. Furthermore, mechanized and automated phoropters are generally required to be of compact construction at low expenditures for material. An optical instrument for manual determination of a patient's deficiencies of sight as disclosed in the U.S. Pat. No. 1,666,406 is an approach to these requirements in which three lens mounting disks are provided with six element sites each. By means of an adding drive the disks are displaced mutually in such a manner that a patient's deficiency of sight can be determined over a wide range in 0.25 dioptre steps. It is, however, not feasible to operate said instrument automatically and, owing to the restricted number of element sites, it is not very versatile.

SUMMARY OF THE INVENTION

It is an object of the present invention to achieve compatibility of partially contradictory requirements such as compactness, scope of application, housing width at the dioptric passage, efficiency and precision of a phoropter in addition to satisfying the kinematic requirements when rotating the lens and prism disks as well as other disks.

BRIEF DESCRIPTIONS OF THE INVENTION

According to the invention this is realized by the features of the first claim. The diameter of the disks supporting spherical and cylindrical lenses, cylinders and optical accessories is substantially the sum of the diameter of the second drive wheel and of twice the diameter of the first drive wheels. When the diameters of the first and the second drive wheels are equal the disk diameters are equal to three-fold the diameter of the drive wheels. Said diameter, in turn, is determined by the free passage of vision and the latter by the eyes under examination. Thus it is feasible to reduce the lens disk diameters by a half without reducing the phoropter efficiency which, on the one hand, involves a lower covering of a patient's face and, on the other hand, favorable kinematic conditions when pivoting the lens and the prism disks. The moment of rotation and the affects of impact and tumbling errors as well as of surface roughnesses of the disks are considerably reduced. The latter, in turn, is a condition that the disks can be arranged closer to one another axially which permits the arrangement of a third disk for the spherical lenses without extending the housing width of the phoropter at the dioptric passage. The drive wheels are preferably embodied as gear wheels or gear rims. It is feasible to drive the two disks which support the cylindrical lenses by only one drive wheel.

It turned out to be geometrically favorable and optically effective when the phoropter comprises, apart from the three disks for the spherical lenses, two disks for the cylindrical lenses, one disk for special elements, and at least one disk for two cross cylinders and two prisms. It is feasible to arrange separate accessories (dark/bright occluders, alignment means) on the disks for the spherical lenses. Typically, the disks are embodied as circles of equal diameter. Since only a part of the element sites of the disk supporting the cross cylinders and the prisms are required it is feasible to embody the disk as a section or as a circle with a sector opening. Each disk has five to eight, preferably six sites for elements, one of which being unoccupied by optical elements for ensuring an optically free vision passage. The disks are preferably arranged in such a manner, considered from the patient's position, that along one axis three disks for the spheric lenses are provided followed by the two disks for the cylindrical lenses, the disks for the special elements and, finally, at least one disk for the cross cylinders and the rotation prisms. The dioptric values which have to be realized by the individual disks behave, particularly concerning the spherical lenses, like 36:6:1 and concerning the cylindrical lenses like 5:1.

Next to the unoccupied element site each lens disk starts with a lens having the lowest dioptre value on the respective disk and which is, from site to site, added to the value of the preceding site. Under the condition that lowest dioptric value of the spheric lenses is 0.25 and that the disks supporting the spheric lenses are freely rotatable relative to one another it is feasible to dial, at 216 possible combinations, the entire dioptric values in 0.25 dioptre steps including zero between +23.25 D. (dioptrics) and −30.5 D. In the same manner it is feasible to set with 25 possible combinations of the cylindrical lenses the values between 0 and −6 D. in 0.25 steps including zero. It is also feasible to obtain the dioptric values between 0 and +6 in the same manner with cylindrical lenses by a conventional combination with spherical lenses.

Since not the entire element sites on the disks supporting the cylindrical lenses are required to determine the dioptric values necessary, it is advantageous to provide the centering cross on the cylindrical lens disk which is in nearest opposition to the patient and the occluder on the cylindrical lens disk being remote from the patient. A spherical lens of −0.125 D., a polarization filter, a Maddox cylinder, color filters, and a hole-shaped aperture, seven elements in all, are provided on the additional disk without extending the disk diameter which is accomplished by the kind of mounting of said individual elements.

DETAILED DESCRIPTION OF THE INVENTION

Figure 1A:
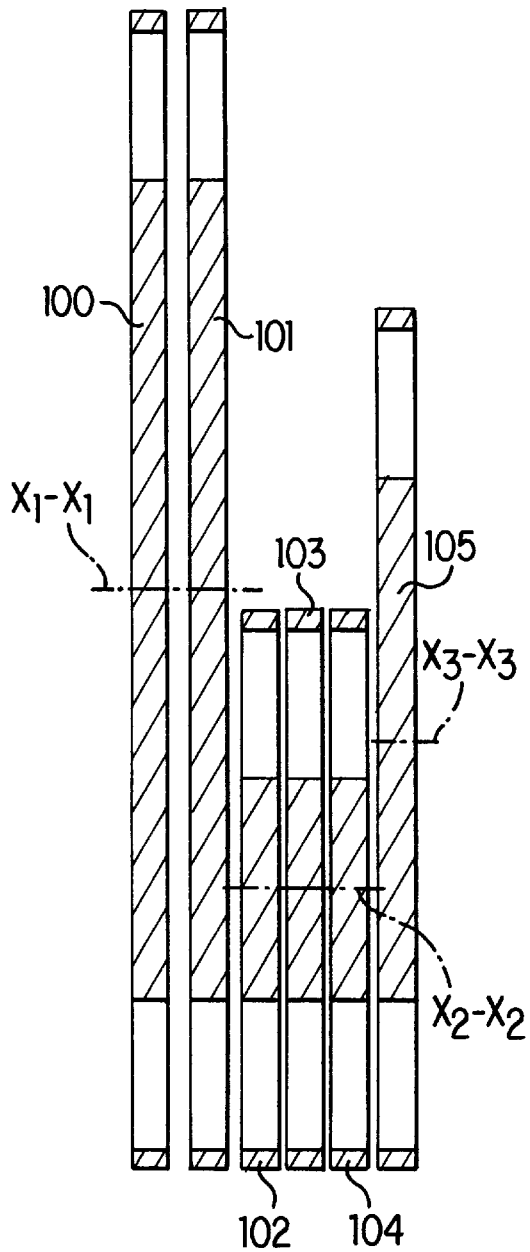
Figure 1B:
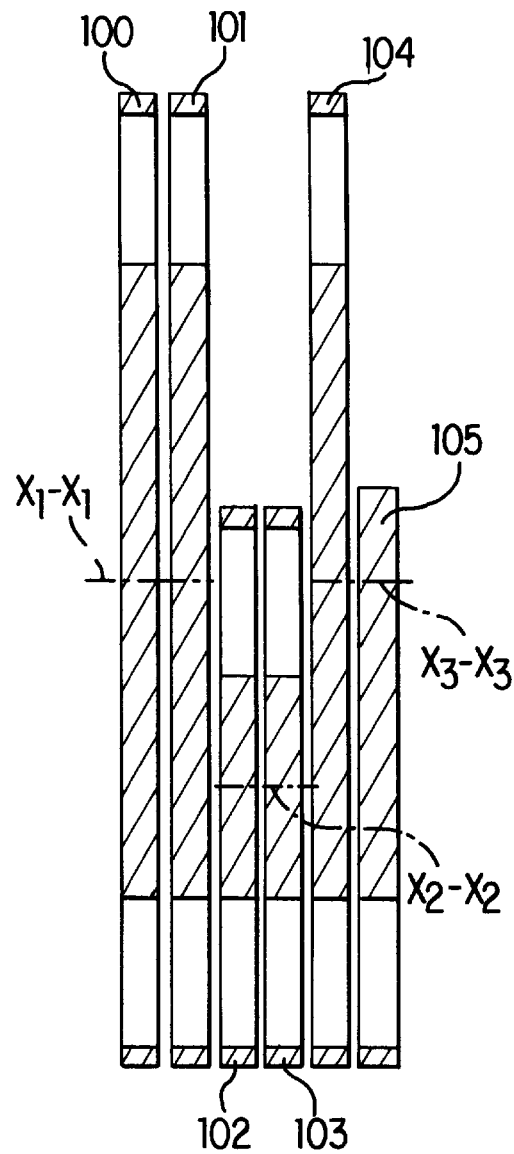
Figure 1C:
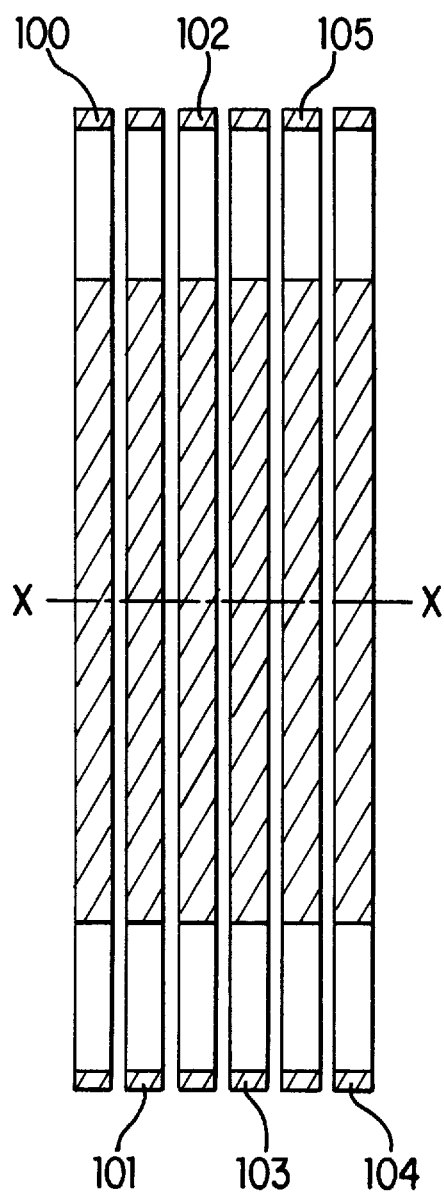
Figure 1D:
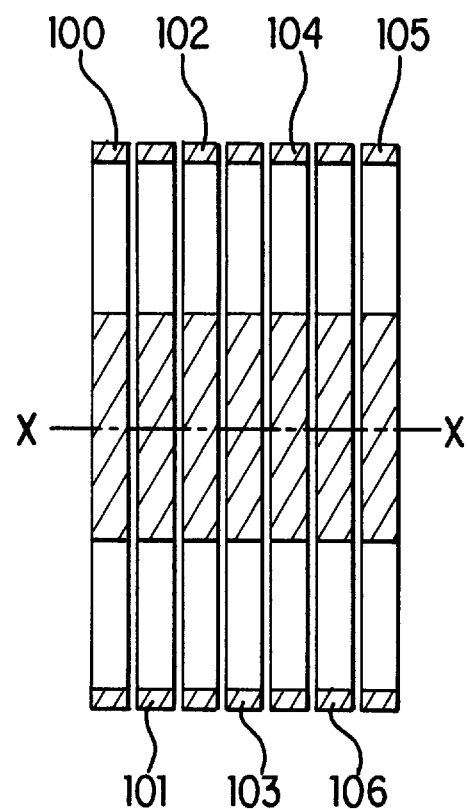
Figure 2:
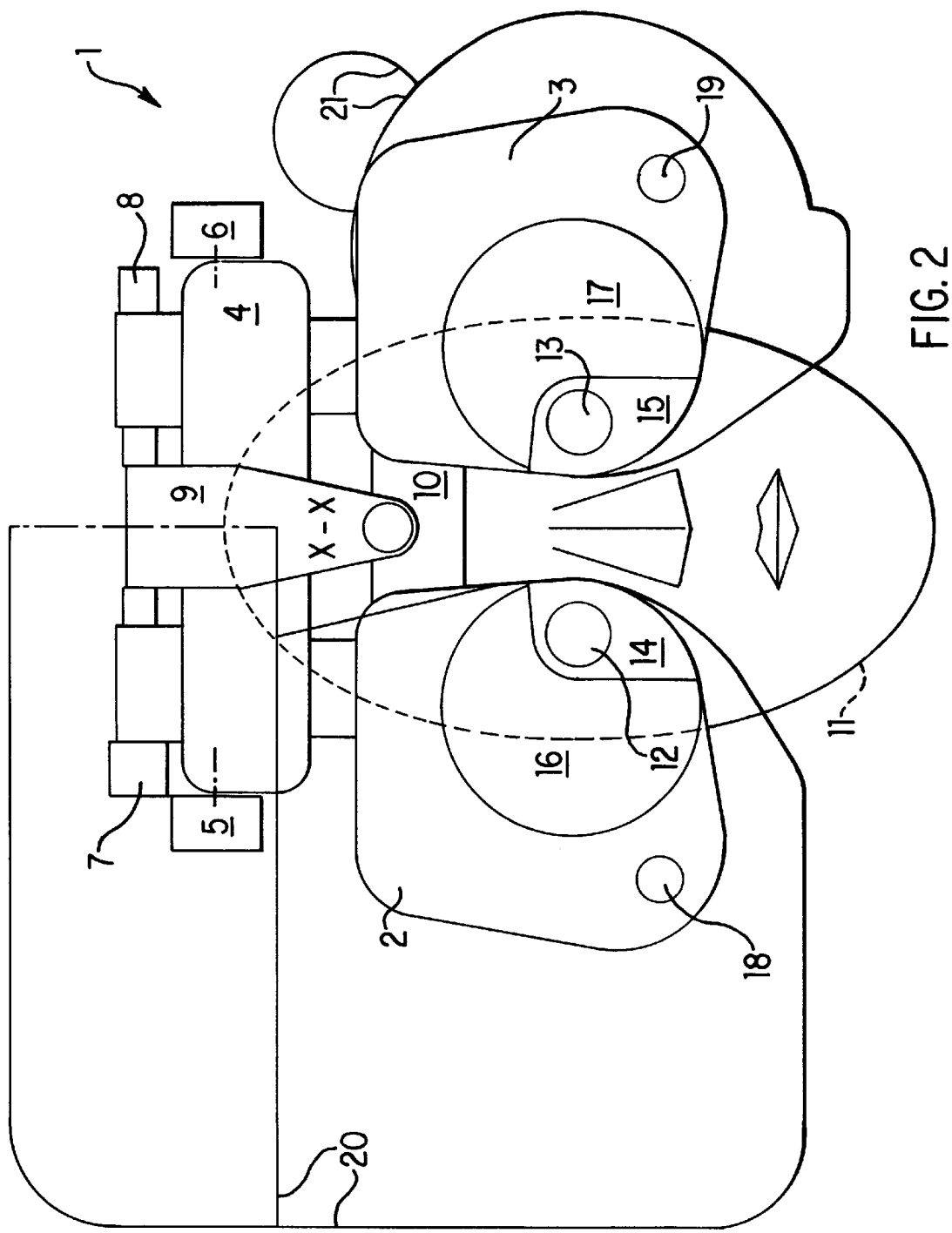
Figure 3:
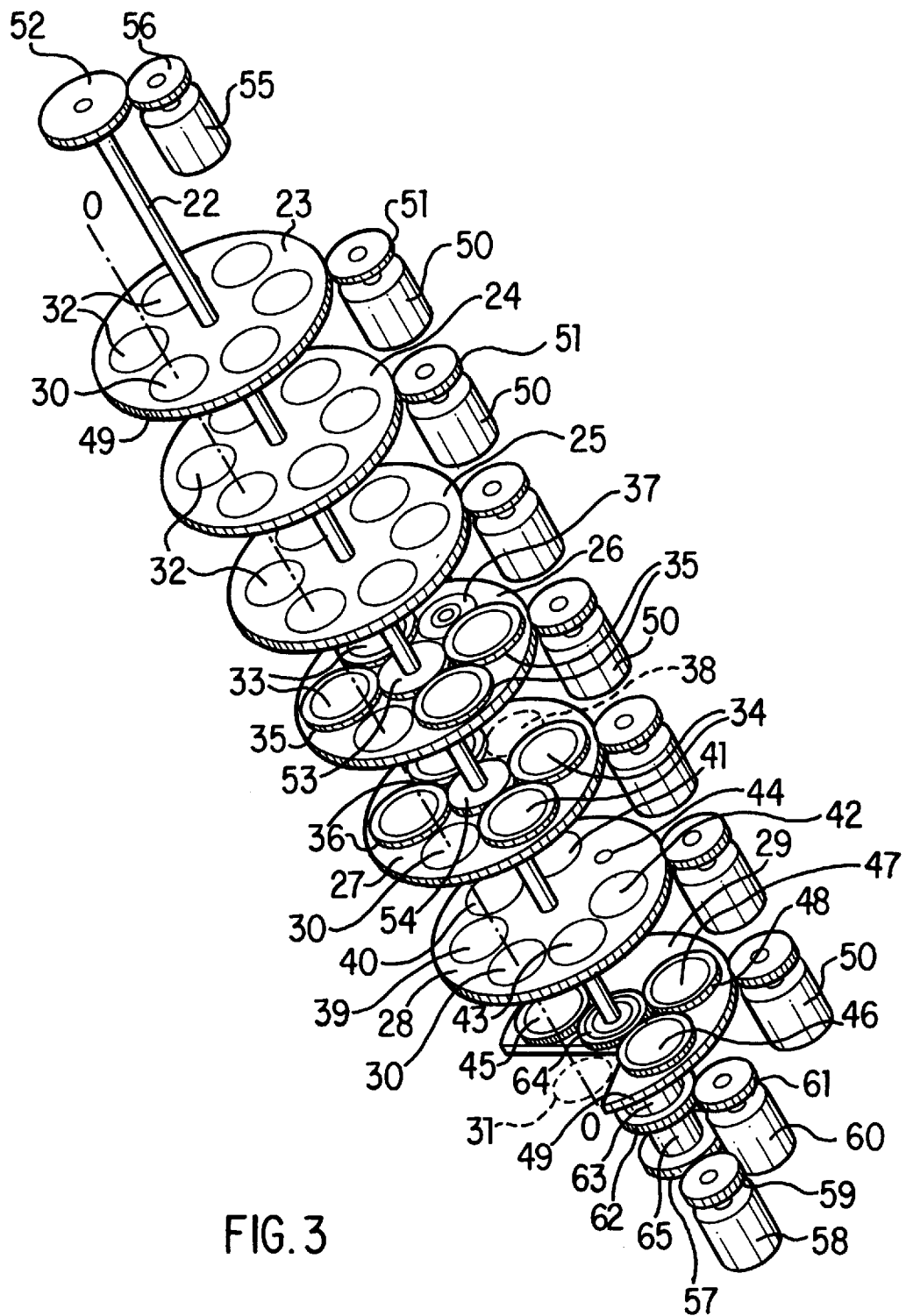

The invention will be explained in more detail by the accompanying schematical drawings and a Table which show and contain, respectively:

in FIGS. 1a to 1d disks in real scale size of different known phoropters compared to the inventional phoropter, in FIG. 2 a view of an inventional phoropter in relation to known phoropters, in FIG. 3 in an exploded view a disk arrangement in a disk housing for the right eye of a patient, and in FIG. 4 the occupation and function of the individual disks in the form of a matrix and Table, respectively.

In FIG. 1a six disks 100 to 105 of a phoropter are shown which satisfies international standards as concerns the scope of values. The disks 100, 101 have a diameter of 155 mm, are each provided with fifteen sites for spherical optical elements and are individually and rotatably seated about an axis $X_1$—$X_1$. The disk diameters are determined by the free opening of the dioptric passage channel (conventionally 19 mm) and by the number of the lens combinations required to cover the the value range necessary of from −30 to +26 dioptrics in 0.25 dioptre steps. The disks 102, 103 have a diameter of 75 mm and are seated for rotation about a second axis $X_2$—$X_2$, so is the equally sized further disk 104 and, typically, possess five sites for elements. The disks 102, 103 are provided with eight cylindrical lenses which can be assembled to combinations. Two cross cylinders and two rotation prisms are mounted on the disk 104, that is, only a part of the element sites is occupied. The disk 105 has a diameter of 115 mm and is provided with ten sites for various accessories and is rotatable about a third axis $X_3$—$X_3$. It is obvious that such a phoropter urgently requires seatings and space.

In FIG. 1b a known manually operated phoropter again is provided with said six disks 100 to 105, the disks 100, 101 of which are of a reduced diameter of 130 mm due to the fact that they only possess twelve sites for spherical lenses, and that on the disk 105 adapted for the accessory elements two spherical lenses are mounted, the latter can be combined with the spherical lenses of the disks 100, 101, as desired, to cover the required range of values. However, these combinations do not permit a cooperation with the remaining elements of the accessory disk 105. The size and the occupation of the disks 102, 103, 104 are substantially the same as in FIG. 1a. In each of the FIGS. 1a to 1d an element site is available on each disk to ensure a free dioptric passage. The disks 104 and 105 of FIG. 1d are mutually exchanged compared to FIG. 1a and the disk 104 is embodied as a sector having two element sites. Though the diameter of the larger disks 100, 101 is slightly reduced compared to FIG. 1a the problems concerning seatings are not solved so that the extension of the phoropter in axial direction exceeds a mechanically determined limit.

In FIG. 1c six equally large disks 100 to 105 of 130 mm diameter which rotate about a common axis X—X are provided each disk has twelve element sites. This is a favorable arrangement as concerns remote controlled or automated phoropters and substantially has no drive problems. The standardization of the disk sizes necessary with this kind of phoropters leads to unoccupied element sites on the disks 102, 103 which involves increased expenditures for material. Furthermore still too large parts of a patient's face are covered. And finally, the seating tolerances for the larger disks 100 to 105 require greater distances between the disks to eliminate mutual obstruction.

FIG. 1d shows the inventional phoropter constituted of seven disks 100 to 106 mounted for rotation about an axis X—X. Each of the disks has a diameter of 75 mm and provides for five to eight element sites. Though seven disks are provided the axial extension of the phoropter is not greater than with the known phoropters since with disks of smaller diameter bearing tolerances lead to a reduced linear staggering. As concerns expenditures for material the inventional solution is far more favorable than the known solutions without any limitation of the application and operation of the inventional phoropter.

In FIG. 2 a phoropter 1 is shown by heavy outlines comprising two disk housings 2 and 3 (right and left) being attached to a mount 4. Two adjustment drives 5, 6 are provided at the mount 4 in parallel to the drawing plane by means of which the mutual space of the disk housings 2, 3 is adjusted, thus it is feasible to vary the distance of pupil. Furthermore, an adjustment drive 7 is provided cooperating with a resilient stop 8 which permits pivoting of the disk housings 2, 3 via an arm 9 and a bridge 10 about an axis X—X at right angles to the drawing plane. Thus it is feasible to take account of different heights of eyes of a patient whose head is shown by an outline 11. Each disk housing 2, 3 is provided with an observation channel 12 and 13, respectively, at right angles to the drawing plane and on the side remote from the patient with recesses 14 and 15, respectively, in the vicinity of the observation channels 12, 13 as well as an elevation 16, 17 extending over the remaining portion of the housing 2, 3. Additionally, a vision passage 18, 19 is provided for a cornea-apex-distance-measurement. Two comparable devices on sale are shown by the light outlines 20, 21, respectively, on plain scale: namely, on the left side of the drawing, a larger motor-driven remote controlled device and, on the right side of the drawing, an exclusively manually operated smaller device. This comparison makes evident that the present invention ensures considerable savings of space and material as well as a favorable vision of a patient's features.

In FIG. 3, in opposition to a patient, seven equally large disks 23 to 29 are seated for rotation on a common axle 22 in such a manner that each disk possesses an unoccupied element site 30 and a sector section 31, respectively, which an observation path of rays defined by an optical axis O—O can pass uninhibitedly along the dioptric observation passage. The diameter of the dioptric observation passage is internationally standardized and is 19 mm. Generally each of the disks 23 to 29 provides for six element sites, the occupation of which is rendered obvious by the Table attached. Apart from the unoccupied element sites 30 for the dioptric observation passage the disks 23, 24, 25 have element sites 32 adapted for five nondisplaceably mounted spherical lenses each. In addition to the free element sites 30 the disks 26, 27 have element sites 33, 34 for four cylindrical lenses each which, in turn, are provided with gear rims 35, 36 and are rotatably seated relative to the disks 26, 27, and furthermore exhibit element sites for one alignment means 37 and one occluder 38, respectively. The diameter of the gear rims (first drive wheels) 35, 36 is determined in dependence on the diameter of the dioptric observation passage and is, for example, 24 mm. The special disk 28 provides for seven element sites, that is, for the dioptric observation passage, for a spherical lens 39 having 0.125 dioptrics, for an A-shaped polarization filter 40, for a V-shaped polarization filter 41, a Maddox cylinder 42, a color filter 43, and an aperture 44. Due to the smallness of these elements it is feasible to mount them on one disk. And finally, the circular sector disk 29, depending on the size of the sector 31, provides for at least three element sites, two of which, in the vicinity of the sector, are employed for mounting cross-cylinders 45, 46 and one of which is adapted to mount two superjacent rotational prisms 47, only one of said prisms being visible in the drawing. The cross-cylinders 45, 46 and the rotation prisms 47 are seated for rotation in the disk plane and, to this end, provided with gear rims 48. Each of the disks 23 to 29 is provided with a gear rim 49 meshing with respective pinions 51 driven by a motor 50. Furthermore, gear wheels 52, 53, 54, rotated by a motor 55 via a pinion 56, are wedged to the axle 22, the gear wheels 53, 54 are meshing the gear rims 35, 36. Thus, by rotating the gear wheel 52 the cylindrical lenses 33, 34, in any case, are rotated about their optical axes in parallel to the plane of the disks. Provided that the diameters of the gear rims 35, 36 and of the gear wheels (second drive wheels) 53, 54 are equal and the gear ratio is unity, then a diameter of 3·24+ 3=75 mm results with respect to the disks 26, 27 and, accordingly, for the entire disks 23 to 29, the fact having been taken into account, that the disks project in diameter the gear rims 35, 36 by 2 mm in order to eliminate any meshing between the pinion 51 and the gear rims 35, 36 as well as for ensuring a sufficient stability of the disks. At the bottom end portion the axle 22 is enveloped by a hollow shaft 65 which, on the one end, is provided with a gear wheel 64 meshing the gear rims 48 and, on the other end, with a gear wheel 57 being engaged with a pinion 59 driven by a motor 58. The one prism of the two rotation prisms 47 arranged subjacent the disk 29 and, therefore, not being visible is driven by a motor 60 via a pinion 61, a gear wheel 62, a second hollow shaft 63 seated upon said first hollow shaft and not shown gear wheels and gear rims, respectively.

It is feasible to position any required element site of each of the disks 23 to 29 in the optical axis O—O by switching ON the respective motor 50. In this manner two-hundred-and-fifteen spheric values in 0.25 dioptre steps can be set by help of the three disks 23, 24, 25. The two disks 26, 27 permit setting of twenty-four cylindrical values in the same steps. The occluder 38 is adapted to shut the observation path of rays O—O, and the centering means serves to align the phoropter to the not shown virtual connecting line eye-visual character chart. The A-polarization filter 40 and the V-polarization filter 41 are employed to separate the test fields for the right eye and the left eye and for determining the stereoscopic vision power of the patient. The Maddox cylinder 42 permits determining and measurement, respectively, of strabism. The color filters 43 (red and green) are means adapted to particular patient conditions in order to determine strabism. The aperture 44 is a kind of artificial iris in order to optimally detect and carry out, respectively, correction, if required, of the central eye lens field. The cross-cylinders 45, 46 enable a balancing of reaction and axes in the course of a sensitive determination of astigmatism, and the rotation prisms serve to determine the amount of strabism in horizontal and vertical direction.

In FIG. 3 drive motors 50, 55, 58, 60 are provided for the disks 23 to 29, as well as for the cylindrical elements 33, 34, 45, 46 and the rotation prisms 47 mounted on them. These elements can be manually rotated in the same manner. Furthermore, it is feasible to provide combinations of manual drives and motor drives. The statements concerning the disk housing 2 in FIG. 2 are also true for the disk housing 3 of FIG. 2.

FIG. 4 shows by means of an easily to follow up tabulated embodiment the occupation of the individual element sites 1 to 6 on the subsequent disks 23 to 29. The entire entered values are to be read in dioptrics. When there is no optically effective element on an element site the "0" is entered. The disks 23 to 25 support spherical lenses, the disks 26 and 27 cylindrical lenses. Since moving components are omitted it is feasible to mount as a seventh element an aperture 44 embodied as a small hole on the same circumference on the disk 28. It is also obvious that the disk 29 is not entirely occupied and therefore can be embodied as a sector so that the "channel vision effect" otherwise disturbing the patient is reduced.

The rotation prisms 47 mounted on the disk 29 are rotatable in opposition to one another so that the deflection of a bundle of rays effected by them cover a range of from zero to a maximum value and they can be commonly rotated so that the deflection may take any desired direction.

LIST OF REFERENCE NUMERALS

1—phoropter
2, 3—disk housing
4—mount
5, 6, 7—adjustment drives
8—resilient stop
9—arm
10—bridge
11, 20, 21—outline
12, 13—observation channel
14, 15—recess
16, 17—elevation
18, 19—vision passage
22—axle
23 to 29, 100 to 106—disk
30, 32, 33, 34—element site
31—sector section
35, 36, 48, 49—gear rim
37—alignment means
38—occluder
39—spherical lens
40—A-shaped polarization filter
41—V-shaped polarization filter
42—Maddox cylinder
43—color filter
44—aperture
45, 46—cross cylinder
47—rotation prism
50, 55, 58, 60—motor
51, 56, 59, 61—pinion
52, 53, 54, 57, 62, 64—gear wheel
63, 65—hollow shaft
O—O, X—X, $X_1$—$X_1$, $X_2$—$X_2$, $X_3$—$X_3$—axis

We claim:

1. A refractor having a housing defining two observation channels for examination of a patients' left and right eyes, said refractor comprising:

two optical element mount disk assemblies respectively disposed in said housing for operation in conjunction with said two observation channels; and each of said two optical element mount disk assemblies including:

optical element mount disks having substantially equal diameters;

said optical element mount disks being coaxially and rotationally arranged about at least one axis;

each of said optical element mount disks having a number of element mounts and optical elements mounted therein, said optical elements including at least one of spherical lenses, cylindrical lenses, cross cylinders and optically effective accessory elements;

at least one of said optical element mount disks being a cylindrical lens mount disk having a number of said cylindrical lenses rotatable mounted in corresponding ones of said element mounts, said number of said cylindrical lenses each having a perimeter drive wheel disposed about a periphery thereof;

said cylindrical lens mount disk having a center drive wheel rotationally disposed at an axis of said cylindrical lens mount disk and engaging said perimeter drive wheels;

said perimeter drive wheels and said center drive wheel having diameters which are substantially equal to each other; and said optical element mount disks having said substantially equal diameters substantially equal to three times said diameter of said center drive wheel.

2. The refractor as claimed in claim 1, wherein two of said optical element mount disks are in the form of said cylindrical lens mount disk and said center drive wheels thereof are commonly driven.

3. The refractor as claimed in claim 2, wherein each of said optical element mount disks has at least five and a maximum of eight of said element mounts.

4. The refractor as claimed in claim 3, wherein an element mount without one of said optical elements mounted therein is provided on each of said element mount disks.

5. The refractor as claimed in claim 1, 2, 3 or 4, wherein one optical element mount disk of said two of said optical element mount disks is provided with an alignment means and another one of said two of said optical element mount disks is provided with an occluder.

6. The refractor as claimed in claim 5, wherein one of said optical element mount disks has seven element mounts.

7. The refractor as claimed in claim 5, wherein one of said optical element mount disks is provided with at least two of said cross cylinders and two rotation prisms and is formed as a sector of a disk.

8. The refractor as claimed in claim 4, wherein said optical element mount disks include three optical element mount disks each having five spherical lenses and an optically effective accessory element.

9. The refractor as claimed in claim 8, wherein of said three optical element mount disks have corresponding ones of said spherical lenses with dioptric values provided in a disk to disk ratio of 1:6:36.

10. The refractor as claimed in claim 3, wherein said two of said optical element mount disks have corresponding ones of said cylindrical lenses with dioptric values provided in a disk to disk ratio of 1:5.

11. The refractor as claimed in claim 1, 2, 3, 4, 9 or 10, wherein one of said optical element mount disks has seven element mounts.

12. The refractor as claimed in claim 11, wherein one of said optical element mount disks is provided with at least two of said cross cylinders and two rotation prisms and is formed as a sector of a disk.

13. The refractor as claimed in claim 1, 2, 3, 4, 8, 9, or 10, wherein one of said optical element mount disks is provided with at least two of said cross cylinders and two rotation prisms and is formed as a sector of a disk.

14. Phoropter as claimed in claim 13, wherein the disk (29) supporting the cross cylinders (45, 46) and two rotation prisms (47) is embodied as a sector.

15. A refractor having a housing defining two observation channels for examination of a patients' left and right eyes, said refractor comprising:

two optical element mount disk assemblies respectively disposed in said housing for operation in conjunction with said two observation channels; and each of said two optical element mount disk assemblies including:

seven optical element mount disks having substantially equal diameters;

said seven optical element mount disks being coaxially and rotationally arranged about at least one axis;

said seven optical element mount disks including first, second and third optical element mount disks each having six element mount positions with five spherical lenses disposed in five of said six element mount positions and a sixth element mount position being unoccupied and defining a through aperture;

said seven optical element mount disks including two cylindrical lens mount disks each having six element mount positions with four cylindrical lenses rotatably mounted in four of said six element mount positions, said four cylindrical lenses each having a perimeter drive wheel disposed about a periphery thereof;

said two cylindrical lens mount disks each having a center drive wheel rotationally disposed at an axis of said cylindrical lens mount disks and engaging said perimeter drive wheels;

said perimeter drive wheels and said center drive wheels having diameters which are substantially equal to each other; and said seven optical element mount disks having said substantially equal diameters substantially equal to three times said diameter of said center drive wheels.

* * * * *